United States Patent [19]

Langer, Jr. et al.

[11] 4,156,603

[45] May 29, 1979

[54] REDUCTIONS WITH CHELATED LITHIUM HYDRIDOALUMINATES OR HYDRIDOBORATES

[75] Inventors: Arthur W. Langer, Jr., Watchung; Thomas A. Whitney, Roselle, both of N.J.

[73] Assignee: Exxon Research & Engineering Co., Florham Park, N.J.

[21] Appl. No.: 849,316

[22] Filed: Nov. 7, 1977

Related U.S. Application Data

[60] Continuation-in-part of Ser. No. 797,766, May 17, 1977, Pat. No. 4,088,666, which is a continuation-in-part of Ser. No. 527,648, Nov. 27, 1974, abandoned, which is a continuation-in-part of Ser. No. 504,152, Sep. 9, 1974, abandoned, which is a continuation-in-part of Ser. No. 344,230, Mar. 23, 1973, Pat. No. 3,933,879, and Ser. No. 462,328, Apr. 19, 1974, which is a division of Ser. No. 276,784, Jul. 31, 1972, abandoned, said Ser. No. 344,230 is a continuation-in-part of Ser. No. 808,328, Mar. 19, 1969, Pat. No. 3,734,963.

[51] Int. Cl.$^2$ .................. C22B 11/04; C22B 15/12; C22B 23/04
[52] U.S. Cl. ................................. 75/0.5 A; 75/108
[58] Field of Search ........................ 75/0.5 A, 108

[56] References Cited

U.S. PATENT DOCUMENTS

| | | | |
|---|---|---|---|
| 3,428,448 | 2/1969 | Bank et al. | 75/108 |
| 3,458,586 | 7/1969 | Langer | 260/668 |
| 3,632,658 | 1/1972 | Halasa | 260/665 |
| 3,661,556 | 5/1972 | Jolley et al. | 75/0.5 AA |
| 3,663,318 | 5/1972 | Little et al. | 75/0.5 AA |
| 3,679,398 | 7/1972 | Geus | 75/108 |
| 3,734,963 | 5/1973 | Langer et al. | 260/563 R |
| 3,758,585 | 9/1973 | Bunting et al. | 260/583 P |
| 3,770,423 | 11/1973 | Lores et al. | 75/108 |
| 3,806,520 | 4/1974 | Haar | 260/326.8 |
| 3,852,262 | 12/1974 | Vit et al. | 260/205 |
| 3,933,879 | 1/1976 | Langer et al. | 252/49.7 R |
| 4,088,666 | 5/1978 | Langer et al. | 260/439 R |

*Primary Examiner*—G. Ozaki
*Attorney, Agent, or Firm*—Joseph J. Allocca

[57] ABSTRACT

This invention relates to the use of chelated lithium hydridoaluminates or hydridoborates in hydride reductions of inorganic substrates. Novel or improved reductions are obtained at increased rates or selectivities in hydrocarbon media to recover metals.

15 Claims, No Drawings

REDUCTIONS WITH CHELATED LITHIUM HYDRIDOALUMINATES OR HYDRIDOBORATES

CROSS-REFERENCE TO RELATED APPLICATIONS

This application is a continuation-in-part of Ser. No. 797,766 filed May 17, 1977, now U.S. Pat. No. 4,088,666, which is a continuation-in-part of Ser. No. 527,648 filed Nov. 27, 1974, now abandoned, which is a continuation-in-part of Ser. No. 504,152 filed Sept. 9, 1974, now abandoned, which in turn is a continuation-in-part of Ser. No. 344,230 filed Mar. 23, 1973 and Ser. No. 462,328 filed Apr. 19, 1974 which is a division of Ser. No. 276,784 filed July 31, 1972, now abandoned; of which Ser. No. 344,230, now U.S. Pat. No. 3,933,879 is a continuation-in-part of Ser. No. 808,328 filed Mar. 19, 1969, now U.S. Pat. No. 3,734,963.

PRIOR ART

The use of lithium aluminum hydride in ether solvents for reductions of unsaturated substrates is well known to those skilled in the art. Ether solvents pose a high degree of fire hazard as well as a strong tendency to form explosive peroxides thus limiting their use in many industrial applications. The present invention is a process for using chelated lithium hydridoaluminates and hydridoborates in hydrocarbon media which overcomes these limitations. Polyaminechelated sodium compounds have been patented separately by one of the present inventors. (U.S. Pat. No. 3,758,585).

THE PRESENT INVENTION

This invention relates to the use of aliphatic, chelating, tertiary polyamines, tertiary aminoethers or polyethers and lithium hydrido compounds in hydride reductions of organic and inorganic substrates in hydrocarbon media. More particularly, this invention relates to an improved reduction process which utilizes hydrocarbon soluble chelated lithium hydridoaluminates or hydridoborates.

The lithium hydrido compounds of this invention have the formula: $MM'H_mY_n$ wherein M is Li, M' is Al or B, Y is a nonreducing group, m is 1 to 4 and n is 0 to 3. The structure of Y is not critical as long as it is unreactive during the reduction process. For example, Y may be hydrocarbyl, halide, alkoxide, secondary amide, mercaptide, other related groups or mixtures thereof. Hydrocarbyl groups normally includes $C_1$–$C_{30}$ alkyl, $C_6$–$C_{30}$ aryl, $C_7$–$C_{30}$ aralkyl, $C_3$–$C_{30}$ naphthenyl, and the like.

Illustrative examples of hydrido compounds include $LiAlH_4$, $LiAlH_3Cl$, $LiAlH_2Br_2$, $LiAlHCl_3$, $LiAlH_3I$, $LiAlH_3OC_4H_9$, $LiAlH_2(C_4H_9)_2$, $LiBH_4$, $LiBH_4$, $LiB_2H_7$, $LiBH(C_2H_5)_3$, $LiBH_2(OC_3H_7)_2$, $LiBH_3Br$, $LiBH_3C_6H_{13}$, $LiBH_3SCH_3$, $LiBH_3N(CH_3)_2$, $LiBH_3C_6H_5$, $LiBH_3CH_2C_6H_5$, $LiBH_3O$-menthyl, $LiBHClC_2H_5(OC_2H_5)$, $LiAlH[N(C_2H_5)_2]_3$, $LiAlH_2[N(C_3H_7)_2]_2$, $LiAlH_3N(C_{10}H_{21})_2$, $LiAlH_3OC_2H_5$, $LiAlH_2BrC_4H_9$, $LiAlH_2N(C_{10}H_{21})_2OC_2H_5$, $LiAlH_3N(C_6H_{11})_2$, $LiAlHBr(i$-$C_4H_9)_2$, $LiAlH_2N(C_2H_5)_2SC_6H_5$, $LiAlH_3SC_8H_{17}$, $LiAlHBrOC_2H_5N(C_{10}H_{21})_2$, $LiAlH_2ISCH_3$, $LiAlH_3OC_6H_5$, $LiAlH_3SC_{20}H_{41}$, $LiAlH_3OC_{20}H_{41}$, $LiAlH_3P(C_6H_{11})_2$ and the like.

Preferred lithium hydridoaluminates and hydridoborates includes $LiAlH_4$, $LiAlH_3Cl$, $LiAlH_2Br_2$, $LiAlH(OC_2H_5)_3$, $LiAlH_3N(CH_3)_2$, $LiAlH_3SCH_3$, $LiAlH_2(O$-1,1,2,2-tetramethylpropyl$)_2$, $LiAlH_2(OC^*H(CH_3)C_6H_5)_2$, $LiAlH_3NHC^*H(CH_3)C_6H_5$, $LiAlH_3(O$-menthyl*), $LiAlH_3(O$-t-$C_4H_9)$, $LiAlH_3OC_6H_5$, $LiAlH_3P(C_6H_{11})_2$, $LiBH_4$, $LiBH_3C_2H_5$, $LiBH_2(C_4H_9)_2$, $LiBH(C_2H_5)_3$, $LiBH_3OC_2H_5$, $LiBH_2(OCH_3)_2$, $LiBH(OCH_2CH_2OCH_3)$, $LiBH_3SC_6H_5$, $LiBH_3N(CH_3)_2$, $LiBH_3(O$-menthyl*), $LiBH_3Cl$, $LiBH_3C_6H_5$, and the like, wherein * denotes optical activity.

The most preferred compounds are $LiAlH_4$ and $LiBH_4$.

The chelating agent is a polyfunctional hydrocarbyl Lewis Base selected from the group consisting of tertiary polyamines, tertiary aminoethers and chelating polyethers.

The chelating agent has one required functionality in a spatial relationship with the other required functionality(ies) in the molecule such that coordinate bonds are established between the functionalities and the lithium cation of the compound.

The tertiary polyamine or aminoether chelating agent may be sparteine, an N,N'-di-($C_1$-$C_4$ alkyl) bispidin, tris-($\beta$-$C_1$-$C_4$-dialkylaminoethyl)-amine, as well as those compounds falling within the scope of the following general formulas:

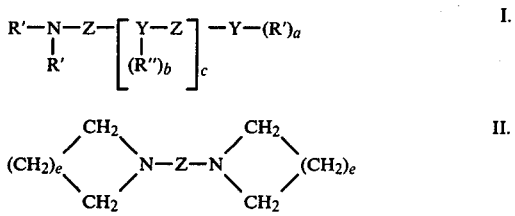

wherein a is 1 or 2, depending on the valence of Y; b is 0 or 1, depending on the valence of Y; c is an integer of 0 to 4, inclusive; e is an integer of 0 to 3, inclusive; R' is the same or different $C_1$-$C_4$ alkyl radical, R'' is the same or different $C_1$-$C_4$ alkyl radical or $C_6$-$C_{10}$ aryl or aralkyl radical; Y is a nitrogen or oxygen atom; and Z is a nonreactive radical selected from the group consisting of (1) $C_4$-$C_{10}$ cycloaliphatic or $C_6$-$C_{10}$ aromatic radicals and their lower alkyl derivatives wherein said radicals are attached to the nitrogen and Y atoms in Formula I and the nitrogen atoms in Formula II at 1,2-positions on the aromatic rings or 1,2- or 1,3-positions on the cycloaliphatic rings; and (2) 2 to 4 methylenic radicals, wherein each methylenic radical contains 0 to 2 monovalent hydrocarbon radicals of 1 to 6 carbon atoms.

Suitable nonlimiting examples of chelating Lewis bases falling within the scope of the above formulas are: N,N,N',N'-tetramethyl-1,2-cyclopentanediamine, N,N,N',N'-tetramethyl-1,2-cyclohexanediamine, (TMCHD, cis, trans, or mixtures), N,N,N',N'-tetramethyl-o-phenylenediamine, 4-ethyl-N,N,N',-N'-tetramethyl-o-phenylenediamine, N,N,N'',N'''-tetramethyl-N'-phenyl diethylene-triamine, N,N,N',N'-tetramethyl-1,2-ethanediamine, (TMED),N,N,N',N'-tetramethyl-1,3-propanediamine, N,N,N',N'',N''-pentamethyl-diethylenetriamine, (PMDT), N,N,N',N'-tetramethyl-1,2-propanediamine, N,N'-dimethyl-N,N'-diethyl1,2-ethanediamine, N,N,N',N'-tetramethyl-1-cyclohexyl-1,2-ethanediamine, N,N,N', N'-tetramethyl-2,3-butanediamine, N,N,N',N'-tetramethyl-1,4-butanediamine, N,N,N',N'',N''',N''''-hexamethyl triethylenetetramine, N,N,N',N'',N''',N'''',N''''', N'''''-octamethylpentaethylenehexamine, beta-(dimethylamino)-ethyl methyl ether, beta-diethylaminoethyl ethyl ether, bis(β-dimethylaminoethyl) ether, beta-(dimethylamino)-ethyl, ethyl ether, gamma-(dimethylamino)-propyl methyl ether, ortho-dimethylamino anisole; 1,2-dipyrrolidylethane, trans-1,2-dipyrrolidyl cyclohexane, 1,2-dipiperidylethane, 1,3-dipyrrolidylpropane, 1,2-dipyrrolidylpropane, 2,2-dimethyl-1,3-dipyrrolidylpropane, 1,1,1-tris-(pyrrolidylmethyl)-ethane, N,N'-dipropyl-9,9-dimethylbispidin.

The chelating polyethers of this invention have the formula:

R'O — Z — [O — Z]$_c$ — O — R' wherein Z, R' and c are the same as defined above.

Suitable nonlimiting examples of chelating polyethers falling within the scope of the above formula are: dimethoxyethane (i.e. glyme), diglyme, triglyme, tetraglyme, trans-1,2-dimethoxycyclohexane, 2,6-dioxydecane, 3,7-dioxynonane, diethylcatechol, 2,5,8-trioxydecane, 7-ethyl-2,5,8-trioxydecane, 4-phenyl-2,5-dioxyhexane, 2,11-dimethyl-4,7,10,1313-tetraoxytetradecane, and the like.

Preferred chelating polyethers includes glyme, diglyme, triglyme or tetraglyme.

Particularly preferred, since they generally give rise to hydrocarbon-soluble complexes and are more stable to decomposition, are the tertiary polyamines (i.e. all of the heteroatoms are tertiary nitrogen atoms) containing at least 5 carbon atoms and at least 2 tertiary nitrogen atoms. Particularly preferred species of the chelating tertiary polyamines are N,N,N',N'-tetramethyl-1,2-ethanediamine (TMED), N,N,N',N'-tetramethyl-1,3-propanediamine (TMPD), N,N,N',N'-tetramethyl-1,2-cyclohexanediamine (cis, trans or mixtures) (TMCHD), N,N,N',N'',N''-pentamethyl diethylenetriamine (PMDT), N,N,N',N'',N''',N'''-hexamethyl triethylenetetramine (HMTT), tris-(β-dimethylaminoethyl)amine (iso-HMTT), heptamethyltetraethylenepentamine (HMTP), octamethylpentaethylenehexamine (OMPH) and higher alkyl derivatives thereof such as the corresponding tris-(β-diethylaminoethyl)amine, dipyrrolidylethane, etc.

Not all lithium compounds form complexes with the above-described chelating agents. It is, however, possible to relate success in chelating said compounds to the lattice energy of the unchelated compounds and to find an approximate cutoff lattice eneregy above which chelation does not occur. This cutoff lattice energy has been experimentally determined to be about 210 kcal/mole for lithium compounds. Since the ability to form chelates is obviously dependent on the chelating agent employed, this cutoff lattice energy is also chelating agent dependent; i.e. only chelating agents capable of forming the most stable complexes will chelate compounds having lattice energies near the upper limits.

A partial list of lithium compounds which chelate is presented in Table A below:

| Lattice Energies | |
|---|---|
| LiCl | 195–206 |
| LiBr | 189–193 |
| LiI | 175–180 |
| LiNO$_3$ | 193–199 |
| LiNO$_2$ | 214 |
| LiN$_3$ | 184–191 |
| LiBH$_4$ | 186 |

Several authors; as compiled in Progr. Solid State Chem., Vol. 1, M.F.C. Ladd, W. H. Lee and H. Reiss, ed., Pergamon Press, London, 1964.

The chelated compounds decompose upon heating to give the unchelated compound as a precipitate and free chelating agent in solution. Upon cooling, this reaction is reversible. The temperature at which the uncomplexed salt precipitates is quite sharp (1°–2°) and reproducible.

The complex of the lithium compound may be readily prepared by mixing the selected compound (having the requisite maximum lattice energy) with the selected chelating agent in the absence of solvent. Such mixing may also be accomplished in the presence of inert hydrocarbons, e.g. C$_4$–C$_{20}$ alkanes (e.g., pentane, heptane, hexadecane); C$_6$–C$_{20}$ aromatics (e.g. benzene, toluene, xylene, dibutylnaphthalene); halogenated aromatics (e.g. chlorobenzene, dichlorobenzene, heterocyclic compounds (e.g. pyridine, thiophene), or mixtures thereof. The most preferred solvents are aromatics and halogenated aromatics such as benzene, toluene, xylene, chlorobenzene, and the like.

The amount of the diluent is not critical and amounts in the range of 0 to 99.9 wt. percent, based on the chelated compound may be conveniently employed. Thus, the chelate may be formed in the absence of solvents, in the form of pastes and in solutions.

Regardless of the method employed the preparation of the chelate is preferably carried out under anhydrous conditions.

The complex may be readily prepared at temperatures from about −100° C. to about 100° C., preferably 0° to 60° C., the latter temperature range is preferred because of convenience and also since higher temperatures favor dissociation of the less stable complexes. Higher temperatures may be used where chelate stability permits; for example, HMTT LiAlH$_4$ is stable to over 200° C. under vacuum. Pressures may range from subatmospheric to 100 psig or more. For convenience sake, atmospheric pressures are preferred.

The molar ratio of lithium compound to chelating agent is preferably 0.1 to 10, and most preferably 1 to 1. However, it should be understood that the amount of chelating agent employed may influence the structure of the resultant chelate. In this regard, it has been found that true chelate formation occurs only with certain specific ratios; that is, if an incorrect ratio (for true compound formation) were employed, the product would have predominantly the composition of the nearest true compound and it would consist of a mixture of several compounds. Although 1:1 complexes are preferred, it is within the scope of this invention to prepare and isolate complexes of other stoichiometries such as 1:2 and 2:1.

Of course, the minimum amount of chelating agent should be that stoichiometric amount required to produce the desired type of chelate (where more than one type of chelate is possible from a particular lithium compound and a particular chelating agent). Where only one type of chelate can be formed or where one is not concerned with the particular type of chelate to be formed (assuming that more than one type is possible), it is desirable to employ amounts of chelating agent in excess of the stoichiometric amount.

Suitable unsaturated substrates include compounds having functional groups such as aldehydes, ketones, esters, α, β, unsaturated carbonyl compounds such as RCH=CH—CO$_2$R' or RCH=CH—CONR'$_2$, thioaldehydes, thioketones, imines, oximes, nitriles, hydrazones, semicarbazides, osazones, aroyl and acyl halides, anhydrides and related compounds. Preferred functional groups in the unsaturated substrate are selected from the group consisting of aldehydes, ketones, esters, imines, oximes, anhydrides and hydrazones. Since R' and R" groups are not critical, some representative, nonlimiting examples are listed for illustrative purposes: benzaldehyde, acetophenone, benzil mono-oxime, butyraldehyde, 2-octanone, octadecyl naphthyl ketone, ethyl cyclohexyl ketone, methyl crotonate, furaldehyde, phenylsulfonylacetone, β-acetylpyridine, thiobenzaldehyde, phenylcyclohexyl thioketone, N-phenylbenzaldimine, phenylacetaldimine, methyl 2-butyl ketoneoxime, ethylpyruvate phenyl hydrazone, glucose phenylosazone, 3-hydroxypropyl methyl ketone, 2-ethoxyethyl methyl ketone, o-dimethylaminobenzaldehyde, 1-ferrocenyl-4-pentanone, $CH_3SO_2CH_2CH_2COCH_3$, $(CH_3)_2PCH_2CH_2CH_2CH_2CH(CH_3)COC_2H_5$, $ClCH_2CH_2CH_2COCH_3$, $(CH_3)_3SiCH_2CH_2COCH_3$, $(CH_3)_3SiCOC_6H_5$, $(CH_3)_3GeCH_2CH_2COCH_3$, $(CH_3)_3SnCH_2CH_2COCH_3$, $C_6H_5COCO_2H$, $CH_3SCH_2CH_2COC_6H_5$, $CH_2=CHCH_2CH_2CH_2COC_6H_{11}$, $CH\equiv CCH_2CH_2COCH(CH_3)_2$,

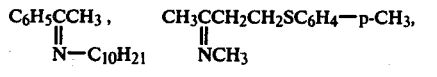

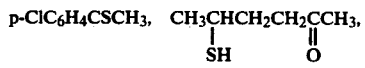

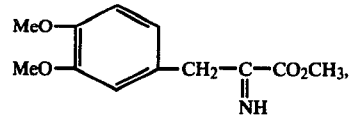

$CH_3CO_2CH_3$, $C_6H_5CO_2C_4H_9$, $C_6H_{11}CO_2CH(CH_3)_2$, $(CH_3CO)_2O$,

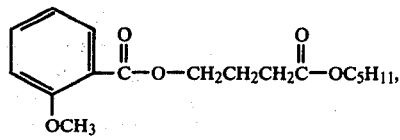

$C_{16}H_{33}CO_2CH_3$, $(C_6H_5CO)_2O$,

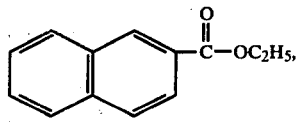

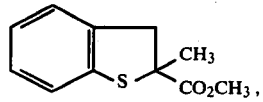

$C_6H_5CH_2CO_2CH_3$, $C_6H_5CH_2CO_2CH_2C_6H_5$,

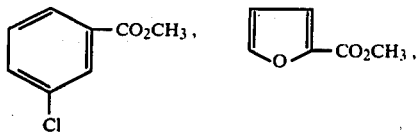

$C_4H_9CO_2C(CH_3)_3$, $CH_3CO_2CH_2CH_2CH_2CH_2CH_2CH_2CO_2CH_3$,

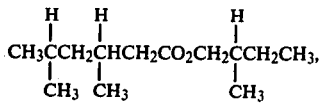

$C_6H_5COCl$, $CH_3COBr$, $C_6H_5CN$, $C_4H_9CN$.

Typical reducible inorganic substrates include the salts of the metals of Groups IVB, VB, VIB, VIIB, VIII, IB, IIB, aluminum, gallium, indium, thallium, germanium, tin, lead, antimony, bismuth and uranium wherein the anion of such salt is selected from the group consisting of Cl, Br, I, F, $NO_3$, CN, $SO_2$, acetate, etc. Suitable nonlimiting examples of reducible inorganic substrates include $CuCl[P(C_6H_5)_3]_2$, $Li_4Fe(CN)_6$, $AuBr_3$, $AuCl_3$, $Ni(NO_3)_2$, $AgNO_3$, $ZnBr_2$, $CdCl_2$, $HgCl_2$, $PdCl_2$, $H_2PtCl_6$, $RhCl_3$, $SnCl_4$, $SbCl_3$, $GaCl_3$, $MnO_2$, $CrCl_3$, $TaF_5$, $TiCl_3$, $UF_6$.

Any inert hydrocarbon solvent may be used for reaction of the chelated hydrides with unsaturated substrates.

This reaction can be carried out in the presence of any hydrocarbon solvent which is inert to the instant chelated hydrides. For example, aromatic hydrocarbons may be used except in those cases where the complex is reactive enough to metalate aromatic compounds. In those cases, saturated hydrocarbon solvents are preferred. The reaction can be run at any convenient temperature, i.e. from $-100°$ to $+200°$ C. but generally lower temperatures, ranging from $-80°$ to $60°$ C. are preferred and most preferred is $0-35°$ C. The upper temperature is usually limited by the stability of complex.

The mole ratio of the chelate to the unsaturated substrate may be in the range of 10:1 to 1:10, preferably 2:1 to 1:2 and most preferably about 1:1 based on the number of hydride functionalities needed to effect reduction.

Pressure is not critical. The reaction can be run at any convenient pressure ranging from subatmospheric to 100 atomspheres, but pressures ranging from 1–10 atmospheres are preferred and most preferred is a pressure of one atomsphere.

A particularly interesting feature of this invention is the ability to achieve novel or improved reductions at increased rates or selectivities in hydrocarbon media. Other advantages will become evident from the examples.

EXAMPLE 1

Into a beaker was put 0.19 g (5 mmole) of $LiAlH_4$, 25 ml of toluene and 0.85 g (5 mmole) of TMCHD and the mixture was stirred one hour at room temperature. The turbid gray mixture was cooled to $-80°$ C. and a solution of 1.20 g (10 mmoles) of acetophenone in 10 ml of toluene was added dropwise while the reaction mixture was maintained at $-70°$ to $-80°$ C. When addition of acetophenone was complete the reaction mixture was maintained at −70° to −80° C. for about 30 minutes and then allowed to warm to 0° C. Water, 5 ml, was added followed by 30 ml of 1N HCl. The liquid phases were separated and the aqueous phase was extracted with 15 ml of pentane. The combined organic phase was then extracted with 15 ml of 1N HCl, 15 ml of 10% NaHCO$_3$ solution, 15 ml of H$_2$O, dried over Na$_2$SO$_4$ and finally concentrated on a rotary evaporator. By vapor phase chromatography (VPC) analysis the product was 92% 1-phenyl-1-ethanol and 7.4% toluene.

EXAMPLE 2

Following the general procedure described in Example 1, a variety of reactions were run using TMCHD.LiAlH$_4$ in toluene. The results of these experiments are summarized in the Table I.

TABLE I

| Substrate | Product |
|---|---|
| C$_6$H$_{13}$COCH$_3$[a] | C$_6$H$_{13}$C(OH)(H)CH$_3$ |
| C$_6$H$_{13}$COCH$_3$[b] | C$_6$H$_{13}$C(OH)(H)CH$_3$ |
| C$_6$H$_5$COC$_4$H$_9$[a] | C$_6$H$_5$C(OH)(H)C$_4$H$_9$ |
| C$_6$H$_{13}$COCH$_3$[b] | C$_6$H$_{13}$C(OH)(H)CH$_3$ |
| α-Tetralone[b] | α-Tetralole |
| β-Tetralone[a] | β-Tetralole |
| C$_6$H$_{13}$COCH$_3$[a,c] | C$_6$H$_{13}$C(OH)(H)CH$_3$ |
| C$_6$H$_5$COH[a,e] | C$_6$H$_5$C(OH)(H)—D |
| C$_6$H$_5$COCOH[d] | C$_6$H$_5$C(OH)(H)CH$_2$OH |
| HOCH$_2$CH$_2$COCH$_3$[a] | HOCH$_2$CH$_2$C(OH)(H)CH$_3$ |
| HO(CH$_2$)$_3$COCH$_3$[a] | HO(CH$_2$)$_3$C(OH)(H)CH$_3$ |

[a]Molar ratio of chelate to substrate = 1:2.
[b]Molar ratio of chelate to substrate = 1:4.
[c]Reaction run at room temperature.
[d]Molar ratio of chelate to substrate = 3:2.
[e]TMCHD . LiAlR$_4$ used for reduction.

EXAMPLE 3

To a 300 ml stirred autoclave was charged 23.33 g (80 mmoles) of N-(2-bromoethyl)phthalimide. The autoclave was evacuated and a solution of 9.12 g (80 mmoles) of trans-1,3-cyclohexanediamine (DACH) in 100 ml of absolute ethanol containing 1 g of C$_{14}$H$_{30}$ was admitted. The autoclave was heated with stirring to 100° C. for 2.5 hours and then to 130° C. for 3 hours whereupon, by VPC analysis of a sample of the reaction mixture, reaction was deemed complete. The reaction mixture was pressured from the autoclave and the latter was washed with 100 ml of absolute ethanol. The combined ethanol solution was evaporated to dryness under reduced pressure affording 30.5 g of crude product to which was added 150 ml of water and 150 ml of 12 N HCl and the mixture was refluxed for 24 hours.

The hydrolysis reaction mixture was cooled in an ice bath and the precipitated phthalic acid was removed by filtration, wt. 12.1 g. The filtrate was evaporated under reduced pressure on a rotary evaporator until no more volatiles could be removed. To the residue was added 86 ml of 90% aqueous formic acid and 20 g of NaHCO$_3$ slowly. The mixture was heated to 80° C. and then 38 ml of 40% aqueous formaldehyde was added dropwise. The reaction mixture was refluxed with stirring for 36 hours, 23 ml of 12 N HCl was added and it was again evaporated under reduced pressure. Water, 50 ml, was added followed by an additional evaporation under reduced pressure. The residue was made basic with excess 50% aqueous NaOH solution and the liberated organic product was recovered by extraction with four 50 ml portions of hexane. Evaporation of the hexane gave a four component crude product which on a solvent free basis was 10.1% A, 80.7% B, 4.2% C and 5.07% D by VPC analysis. Component B was identified as TMCHD.

The above experimental procedure was repeated using 9.12 g of DACH and 40.66 g of N-(2-bromoethyl) phthalimide followed by 115 ml of formic acid, 27 g of NaHCO$_3$ and 50 ml of formaldehyde for the Eschweiler-Clarke methylation step. The crude methylated product had a similar composition as the first run by VPC analysis.

The crude products from both runs were combined and distilled. Cut I, bp 68° C. at 3.5 mm, wt. 11.9 g; Cut II bp 69° C. at 3.4 mm, wt. 3.4 g; and Cut III bp 70–99° C. at 3.4–1.4 mm, wt. 5.4 g were obtained. VPC analysis gave the following compositions: Cut I 0.5% A, 90.9% B, 4.5% C and 0.3% D; Cut II 0.6% A, 91.7% B, 6.4% C and 0.3% D; and Cut III 0.5% A, 29.4% B, 7.5% C and 61.7% D.

To Cut III, wt. 5.4 g, was added 9.73 g of n-hexane and 2.20 g of NaI and the mixture was stirred. Periodic VPC analysis indicated that the amount of component D remaining in solution was decreasing. After 18 hours, the mixture was filtered and the solid residue, wt. 4.76 g, was added to excess aqueous NaOH solution and the mixture extracted with three 25 ml portions of hexane. The combined extract was dried and the hexane was stripped under vacuum. A clear colorless liquid remained, wt. 2.58 g which by VPC analysis was 99+% pure D. This material was shown to be trans-N-(β-dimethylaminoethyl)-N,N', N'-trimethyl-1,2-cyclohexanediamine (β-DMAE-tri-MCHD) by 100 MH$_z$ NMR spectroscopy and elemental analysis: Theory for C$_{13}$H$_{29}$N$_3$; C, 68.67%, H, 12.85%; N, 18.48%. Found: C, 69.32%; H, 13.00%; N, 17.36%.

To 20 ml of toluene was added 1.93 g of β-DMAE-tri-MCHD and 0.45 g of LiAlH$_4$, the mixture was stirred overnight at room temperature and was then filtered. Evaporation of a portion of the filtrate gave a white solid which was β-DMAE-tri-MCHD.LiAlH$_4$, wt. 0.32 g. The remainder of the filtrate, estimated to contain about 6 mmoles of β-DMAE-tri-MCHD was cooled to −80° C. and 2.12 g (16.5 mmoles) of 2-octanone dissolved in enough toluene to make 20 ml was gradually added over an hour with stirring. The reaction mixture was maintained at −75° to −80° C. for 15 minutes and then allowed to slowly warm to 0° C. Ice was added and gas was evolved. Then 55 ml of 0.5 N HCl was added, the organic phase was separated, washed with 15 ml of NaHCO$_3$ solution and 15 ml of water. After drying over Na$_2$SO$_4$, the toluene was stripped from the product under reduced pressure. The resultant oil, free of 2-octanone by VPC analysis was pure 2-octanol.

EXAMPLE 4

A 1.09 g (3 mmole) portion of phenyl triphenylsilyl ketone [C$_6$H$_5$COSi(C$_6$H$_5$)$_3$] was dissolved in 20 ml of toluene and the solution was cooled to −75° C. To the cold, stirred solution was added 1.5 mmoles of TMCHD.LiAlH$_4$ as a solution in toluene dropwise with stirring. After addition of the TMCHD.LiAlH$_4$ solution was complete, the reaction mixture was stirred at −80° to −75° C. for 30 minutes and then allowed to warm to 0° C. whereupon it was hydrolyzed with ice and 20 ml of 1 N acetic acid. The organic layer was separated, extracted twice with 20 ml portions of 1 N HCl, once with 20 ml of saturated NaHCO$_3$ solution, once with 20 ml of water and was then dried over Na$_2$SO$_4$. Evaporation of toluene under reduced pressure gave an oil which solidified when scratched with a spatula. The product was C$_6$H$_5$CHOHSi(C$_6$H$_5$)$_3$, wt. 1.1 g.

EXAMPLE 5

To 210 ml of 1.0 M LiAlH$_4$.PMDT (0.21 mole in benzene) was added dropwise a solution of 45.5 g diethyl hexahydrophthalate. A vigorous reaction occurred and the flask was cooled to maintain the temperature at 30–40° C. After addition, the reaction mixture (pasty) was refluxed for about 3 hours. The mixture was cooled and hydrolyzed with 10% hydrochloric acid. The benzene solution was separated and the aqueous phase was washed with three 200 ml portions of ether. The combined benzene solution and ether extracts were washed with water and sodium bicarbonate solution and dried over anhydrous Na$_2$SO$_4$.

The solution was filtered and ether-benzene was stripped off. The residue was simply distilled under reduced pressure. A product was collected (b.p. 123–125° C. at 0.5 mm, wt. 17.0 g) which solidified on standing. Residue = 3.2 g.

Infrared analysis showed a broad OH band at about 3300 cm$^{-1}$ and no carbonyl band at 1740 cm$^{-1}$, gas chromatography (G.C.) analysis showed product to be 93% pure trans-1,2-cyclohexanedimethanol.

A number of additional runs were made using benzene solutions of PMDT in various mole ratios to LiAlH$_4$, TMED as the chelating agent and hexahydrophthalic anhydride instead of diethylhexahydrophthalate as the substance to be reduced. The data from these experiments are summarized in Table II, Reaction times varied from two to 18 hours, but even a reaction time of 2 hours is probably unnecessary. Reduction appeared to be complete within minutes.

In contrast to the results summarized in Table IV, reduction of diethyl hexahydrophthalate or hexahydrophthalic anhydride with excess LiAlH$_4$ by conventional procedures in ether solvents gave impure glycol in very low yield only after extended reaction times.

Clearly, chelated LiAlH$_4$ in benzene is a far superior reducing agent to LiAlH$_4$ in ether solvents. Yields are higher, incomplete reductions are avoided and reaction times are an order of magnitude or more shorter.

TABLE II

| Run | Chelating agent and mole ratio to LiAlH$_4$ | Reaction time hrs. | Chel. LiAlH$_4$ preformed | Compound reduced, g.(moles) | LiAlH$_4$ g. | Yield of distilled product, percent | Percent of purity of product |
|---|---|---|---|---|---|---|---|
| 1 | PMDT 1:1 | 3 | Yes | Diester 45.5 (0.2) | 8.0 | 59 | 93 |
| 2 | PMDT 1:1 | 3 | Yes | Anhydride 30.8 (0.2) | 8.0 | 28 | 93 |
| 3 | PMDT 0.25:1 | 4 | No | Anhydride 77 (0.5) | 21.8 | 30 | 91 |
| 4 | PMDT 0.5:1 | 4 | No | " | 21.8 | 34 | 90 |
| 5 | PMDT 0.75:1 | 4 | No | " | 21.8 | 38 | 91 |
| 6 | PMDT 1:1 | 4 | No | " | 21.8 | 29 | 88 |
| 7 | TMED 1:1 | 4 | No | " | 21.8 | 39 | 90 |
| 8 | TMED 1:1 | 2 | No | Diester 2,215(9.7) | 424.2 | 81 | 96 |
| 9 | None[a] | 24 |  | Diester 2,652(11.6) | 445 | 30 | [b]89 |

[a]Solvent:diethyl ether rather than benzene.
[b]Runs 1–8 distilled in simple one-plate column; run 9 distilled in 45-plate spinning band column.

Examples of Inorganic Substrate Reduction Using Chelated Lithium Hydrido Aluminates or Hydridoborates

EXAMPLE 6

About 0.24 grams (∼1 mM) Li$_4$Fe(CN)$_6$ was added to 2 ml (1 mM) LiAlH$_4$.PMDT solution. A vigorous evolution of large volumes of gas (>20 ml) resulted and the temperature rose to ∼50° C. A turbid liquid containing a whitish solid was obtained. An additional 2 ml (1 mM) LiAlH$_4$.PMDT solution was added, accompanied by additional vigorous bubbling and reaction. 2 ml (1 mM) more solution was added. The system was stirred overnight at room temperature. Upon cessation of stirring the system was allowed to stand. A colorless liquid with fine greyish solids was obtained.

EXAMPLE 7

1.31 grams (5mM) (C$_6$H$_5$)$_3$P was put into a 125 ml stoppered Erlenmeyer flask along with 25 ml benzene. 0.25 grams (2.5 mM) CuCl and an additional 25 ml benzene was added to the flask with stirring and stirred for about 5 minutes. An almost clear, faintly green solution was obtained.

2.5 ml (2.5 mM) LiAlH$_4$.PMDT was added dropwise to the above solution. The first few drops turned the solution orange then quickly to brownish-black opaque. A granular type solid appeared and some gas was evolved. There was no noticeable temperature rise. The solution was stirred overnight. Upon cessation of stirring, the solution turned almost clear light brown with a dark sediment at the bottom. The walls of the flask had a slight copper mirror. The solution was filtered through a filter dish (ASTM 10–15) and the solid was washed with benzene and dried by drawing N$_2$ through it. A fine black powder was recovered weighing 0.36 grams. The filtrate was concentrated using a vacuum and rotary evaporator at room temperature. A white granular solid residue wet with a clear brownish-yellow liquid was recovered, total weight 2.02 grams, material dissolved and diluted in benzene to 10 ml (volumetric flask).

A portion of the fine black powder was analyzed: 14.89% C.; 2.81% H; 2.74% N and 11.0% Cl.

Another portion of the fine black powder was dispersed in pentane and hydrolyzed in water-vigorous gas evolution. A black insoluble material resulted which was analyzed: 3.37% Li; 16.71% Al and 41.71% Cu.

EXAMPLE 8

1.09 Grams (2.5 mM) $AuBr_3$ was put into a 50 ml Erlenmeyer flask along with a magnetic stirring bar. 25 ml benzene was added resulting in an immediate dark brown coloring to the benzene. The mix quickly became opaque. The mix was stirred 0.5 hr at room temperature. The walls of the flask took on a yellow coating. The mix was filtered through a filter dish (ASTM 10–15). The filtrate was an opaque brown liquid. Brownish-yellow residue weighing 1.08 grams was recovered.

25 ml benzene was added to the residue yielding an opaque brown mix. To this was added 0.65 grams (2.5 mM) LiBrPMDT, which caused the mix to turn reddish brown. This mix was allowed to stir 0.5 hr at room temperature, then filtered through a filter dish (ASTM 10–15). The filtrate (A) was a clear, deep red which slowly turned turbid. The residue was washed with 35 ml benzene resulting in 0.93 grams of a brownish-yellow solid, and a second filtrate (B). To filtrate (A) was added 0.5 ml (0.5 mM) $LiAlH_4$.PMDT which resulted in an apparent reaction, the evolution of small bubbles and a solid is formed. Allowed to stand at room temperature, the liquid slowly evaporated leaving a residue.

The same procedure was used on filtrate (B) which immediately turned opaque brown with some vigorous gas evolution.

EXAMPLE 9

3.5 ml (3 mM) LiCl.PMDT was diluted to 25 ml with benzene in a 50 ml flask. 0.91 grams (3 mM) $AuCl_3$ was added to the solution slowly with stirring. A purple solid in a clear colorless liquid was obtained which solid slowly changed from purple to a cloudy light brown solid. The solution was stirred vigorously for 0.5 hour at room temperature. The solution settles out on standing to a clear almost colorless liquid, a curdy light brown solid and a small amount of unreacted $AuCl_3$. 3 ml $LiAlH_4$.PMDT was slowly added to the mix. Immediate reaction with the mix turning dark brown-black with a substantial amount of gas evolution. Mix stirred at room temperature for 0.5 hour. On standing, mix settles out as a clear colorless solution with a black solid. The solid is filtered out in a dish (ASTM 10–15) and washed with 25 ml benzene and then 10 ml pentane leaving a fine black powder (0.8 gm). Filtrate, clear light yellow is discarded. When exposed to air the fine black powder reacts leaving a black solid. The fine black powder has a particle size of 1μ and assayed as 3.60% C.; 0.66% H and 1.36% N. with a major amount of gold and aluminum and a minor amount of lithium.

EXAMPLE 10

1.31 gms (5 mM) $(C_6H_5)_3$ P was put into a 125 ml stoppered Erlenmeyer flask along with 25 ml benzene. To this was added 0.25 grams (2.5 mM) CuCl and another 25 ml benzene. The mix was allowed to stir about 20 minutes resulting in an almost clear, faintly green solution. To this solution was added 3.33 ml (2.5 mM) $LiAlH_4$.TMED dropwise. Solution turned orange as first drops added. Color gradually deepened to muddy brown with some sticky, blackish brown material adhering to bottom of flask, with a lighter nonsticky brown solid dispersed in solution. This was stirred 2 minutes then permitted to settle resulting in a clear, faintly brown solid with a brown sediment (some gas evolution was noted). This solution was filtered (ASTM 10–15 filter dish) and the recovered solid washed in benzene (5 ml) and dried in $N_2$. The solid weighed 0.33 grams. A small sample of the filtrate was permitted to evaporate yielding a white solid residue which evolved gas when some methanol was added. The solid was analyzed: 20.3% C., 3.62% H. and 4.80% N.

0.0569 Grams of the solid was dispersed in pentane and hydrolyzed in methanol (vigorous bubbling) then $H_2O$ plus dilute sulfuric acid. Some blue color observed in aqueous layer. The black particles did not readily dissolve. Assayed as 2.06% Li, 36.9% Cu and 8.74% Al.

EXAMPLE 11

12.78 Grams (60.5 mM) $LiAlH_4$.PMDT was dissolved in 240 ml benzene in a 4 neck 500 ml round bottom flask yielding a colorless, slightly hazy solution. 2 grams (~5.7 mM nickel) $Ni(NO_3)_2/SiO_2$ was added to this solution over a 5 minute period. As the light green $Ni(NO_3)_2/SiO_2$ solid contacted the solution gas was evolved and the solid turned black. At completion of addition mix is a dark slurry. Temperature rose from 26 to 30° C. After 0.5 hours, mixing temperature still 30° C. and gas still being evolved. Mixture allowed to stir overnight at room temperature. Temperature next day was 26° C. Liquid is black opaque. One-half of the mixture removed and filtered through a fritted disk (ASTM 10–15) and residue washed several times with 10 ml portions of benzene. Solid residue dried in drawn $N_2$. Fine dark brown powder 1.52 grams and clear deep orange brown filtrate. Brown powder treated at room temperature and 0.1 mm Hg pressure for 2 hours. Weight of powder now 1.42 grams. This material was reactive to water. The second half of the mixture was heat treated at 80° C. and was filtered and washed as above resulting in a fine dark brown powder which weighed 1.56 grams and a clear deep orange brown filtrate. This powder was treated at room temperature and 0.1 mm Hg pressure for 2 hours and weight 1.44 grams. This material, on a frit, was found to be pyrophoric.

What is claimed is:

1. A process for reducing inorganic substances which comprises the step of reacting a reducible inorganic substrate with a chelate compound, said chelate compound formed by mixing a lithium hydrido compound and a chelating polyfunctional hydrocarbyl Lewis base in an inert hydrocarbon medium at −100° to +200° C., and recovering metals.

2. The process according to claim 1 wherein the lithium hydrido compound is of the formula $MM'H_mY_n$, wherein M is Li, M' is Al or B; m is 1 to 4 and n is 0 to 3; Y is a nonreducing, unreactive group.

3. The process according to claim 1 wherein the chelate compound is tetramethylcyclohexanediamine.-$LiAlH_4$.

4. The process according to claim 1 wherein the chelate compound is tetramethylethanediamine.-LiAlH$_4$.

5. The process according to claim 1 wherein the chelate compound is pentamethyldiethylenetriamine.-LiBH$_4$.

6. The process according to claim 1 wherein the chelate compound is tetramethylethanediamine.LiBH$_4$.

7. The process according to claim 1 wherein the lithium hydrido compound is LiAlH$_4$.

8. The process according to claim 1 wherein the lithium hydrido compound is LiBH$_4$.

9. The process according to claim 1 wherein the chelating polyfunctional hydrocarbyl Lewis base is selected from the group consisting of tertiary polyamines, tertiary aminoethers, chelating polyethers, sparteine, N,N'-di-(C$_1$-C$_4$ alkyl) bispidin, tris- (β-C$_1$-C$_4$-dialkylaminoethyl)-amine and those compounds having the formulas:

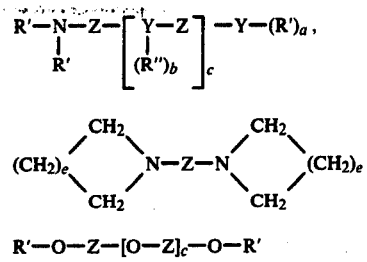

$$R'-O-Z-[O-Z]_c-O-R' \quad \text{III}$$

wherein a is 1 or 2, depending on the valence of Y; b is 0 or 1, depending on the valence of Y; c is an integer of 0 to 4 inclusive; e is an integer of 0 to 3 inclusive; R' is the same or different C$_1$-C$_4$ alkyl radical, R'' is one selected from the group consisting of C$_1$-C$_4$ alkyl, C$_6$-C$_{10}$ aryl or aralkyl radical; Y is a nitrogen or oxygen atom; Z is a nonreactive radical selected from the group consisting of:

(1) C$_4$-C$_{10}$ cycloaliphatic or C$_6$-C$_{10}$ aromatic radicals and their lower alkyl derivatives wherein said radicals are attached to the nitrogen and Y atoms in Formula I, the nitrogen atoms in Formula II and the oxygen atoms in Formula III at 1,2-positions on the aromatic rings or 1,2- or 1,3-positions on the cycloaliphatic rings; and (2) 2 to 4 methylenic radicals, wherein each methylenic radical contains 0 to 2 monovalent hydrocarbon radicals of 1 to 6 carbon atoms.

10. The process according to claim 1 wherein the chelating polyfunctional hydrocarbyl Lewis base is glyme.

11. The process according to claim 1 wherein the chelating polyfunctional hydrocarbyl Lewis base is diglyme.

12. The process according to claim 1 wherein the chelating polyfunctional hydrocarbyl Lewis base is triglyme.

13. The process according to claim 1 wherein the chelating polyfunctional hydrocarbyl Lewis base is tetraglyme.

14. The process according to claim 1 wherein the inert hydrocarbon medium is an aromatic.

15. The process according to claim 1 wherein the inert hydrocarbon medium is a halogenated aromatic.

* * * * *